(12) United States Patent
Bischoff et al.

(10) Patent No.: US 7,586,623 B2
(45) Date of Patent: Sep. 8, 2009

(54) OPTICAL METROLOGY OF SINGLE FEATURES

(75) Inventors: Joerg Bischoff, Illmenau (DE); Xinhui Niu, San Jose, CA (US); Junwei Bao, Palo Alto, CA (US)

(73) Assignee: Tokyo Electron Limited, Tokyo (JP)

( * ) Notice: Subject to any disclaimer, the term of this patent is extended or adjusted under 35 U.S.C. 154(b) by 24 days.

(21) Appl. No.: 12/127,640

(22) Filed: May 27, 2008

(65) Prior Publication Data

US 2008/0259357 A1 Oct. 23, 2008

Related U.S. Application Data

(63) Continuation of application No. 11/404,645, filed on Apr. 14, 2006, now Pat. No. 7,379,192, which is a continuation of application No. 10/853,060, filed on May 24, 2004, now Pat. No. 7,030,999, which is a continuation of application No. 10/175,207, filed on Jun. 18, 2002, now Pat. No. 6,775,015.

(51) Int. Cl.
*G01B 11/24* (2006.01)
(52) U.S. Cl. .................. 356/602; 356/369; 356/609; 356/625
(58) Field of Classification Search ........... 356/369, 356/602–609
See application file for complete search history.

(56) References Cited

U.S. PATENT DOCUMENTS

| 5,703,692 | A | 12/1997 | McNeil et al. |
| 5,867,276 | A | 2/1999 | McNeil et al. |
| 5,880,838 | A | 3/1999 | Marx et al. |
| 6,034,378 | A | 3/2000 | Shiraishi |
| 6,049,220 | A | 4/2000 | Borden et al. |
| 6,130,750 | A * | 10/2000 | Ausschnitt et al. .......... 356/401 |
| 6,137,570 | A | 10/2000 | Chuang et al. |
| 6,172,349 | B1 * | 1/2001 | Katz et al. ............... 250/201.3 |
| 6,396,628 | B1 | 5/2002 | Osa et al. |
| 6,429,943 | B1 | 8/2002 | Opsal et al. |
| 6,633,831 | B2 | 10/2003 | Nikoonahad et al. |
| 6,775,015 | B2 | 8/2004 | Bischoff et al. |

(Continued)

FOREIGN PATENT DOCUMENTS

JP 01-145504 A 6/1989

(Continued)

OTHER PUBLICATIONS

Japanese Office Action mailed Oct. 21, 2008, for JP Application No. 2004-513691, 4 pages. (English translation attached, 7 pages).

(Continued)

*Primary Examiner*—Gregory J Toatley, Jr.
*Assistant Examiner*—Iyabo S Alli
(74) *Attorney, Agent, or Firm*—Manuel B. Madriaga (57) ABSTRACT

The profile of a single feature formed on a wafer can be determined by obtaining an optical signature of the single feature using a beam of light focused on the single feature. The obtained optical signature can then be compared to a set of simulated optical signatures, where each simulated optical signature corresponds to a hypothetical profile of the single feature and is modeled based on the hypothetical profile.

20 Claims, 7 Drawing Sheets

U.S. PATENT DOCUMENTS

| | | |
|---|---|---|
| 7,030,999 B2 | 4/2006 | Bischoff et al. |
| 7,106,425 B1 | 9/2006 | Bultman et al. |
| 7,379,192 B2 | 5/2008 | Bischoff et al. |
| 2002/0191171 A1* | 12/2002 | Nishi .................. 250/492.2 |

FOREIGN PATENT DOCUMENTS

| | | |
|---|---|---|
| JP | 09-092596 A | 4/1997 |
| JP | 11-133308 A | 5/1999 |
| JP | 2000-009443 A | 1/2000 |
| JP | 2001-267211 A | 9/2001 |

OTHER PUBLICATIONS

Bischoff, J. et al. (Jul. 1997). "Single Feature Metrology by Means of Light Scatter Analysis," *Proceedings of SPIE* 3050:574-585.

International Search Report mailed Mar. 2, 2004, for PCT Application No. PCT/US2003/18186 filed Jun. 9, 2003, 3 pages.

Jenkins, F. A. et al. (1957). *Fundamentals of Optics.* 3rd Edition, McGraw-Hill: New York, pp. 306-308.

\* cited by examiner

OPTICAL METROLOGY OF SINGLE FEATURES

CROSS REFERENCE TO RELATED APPLICATIONS

This application is a continuation application of U.S. patent application Ser. No. 11/404,645, filed Apr. 14, 2006, now issued as U.S. Pat. No. 7,379,192, which is a continuation application of U.S. patent application Ser. No. 10/853,060, filed May 24, 2004, now issued as U.S. Pat. No. 7,030,999, which is a continuation of U.S. patent application Ser. No. 10/175,207, filed Jun. 18, 2002, now issued as U.S. Pat. No. 6,775,015, all of which are incorporated herein by reference in their entireties for all purposes.

BACKGROUND

1. Field of the Invention

The present invention relates to wafer metrology, and more particularly to optical metrology of single features.

2. Related Art

In semiconductor manufacturing, periodic gratings are typically utilized for quality assurance. For example, one typical use of such periodic gratings includes fabricating a periodic grating in proximity to a semiconductor chip. By determining the profile of the periodic grating, the quality of the fabrication process utilized to form the periodic grating, and by extension the semiconductor chip proximate the periodic grating, can be evaluated.

The profile of a periodic grating can be determined using optical metrology. In general, optical metrology involves directing an incident beam at the periodic grating, and measuring the resulting diffraction beam. However, in conventional optical metrology, multiple periods of the periodic grating are typically illuminated. Thus, the determined profile for the periodic grating is more of an average representation of the illuminated periods rather than of an individual period.

SUMMARY

In an exemplary embodiment, the profile of a single feature formed on a wafer can be determined by obtaining an optical signature of the single feature using a beam of light focused on the single feature. The obtained optical signature can then be compared to a set of simulated optical signatures, where each simulated optical signature corresponds to a hypothetical profile of the single feature and is modeled based on the hypothetical profile.

DESCRIPTION OF DRAWING FIGURES

The present invention can be best understood by reference to the following description taken in conjunction with the accompanying drawing figures, in which like parts may be referred to by like numerals:

FIGS. 7-A and 7-B depict a source and detector pair with pupil stops;
FIGS. 8-A and 8-B depict a source and detector pair with pupil stops;

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

Figure 1:
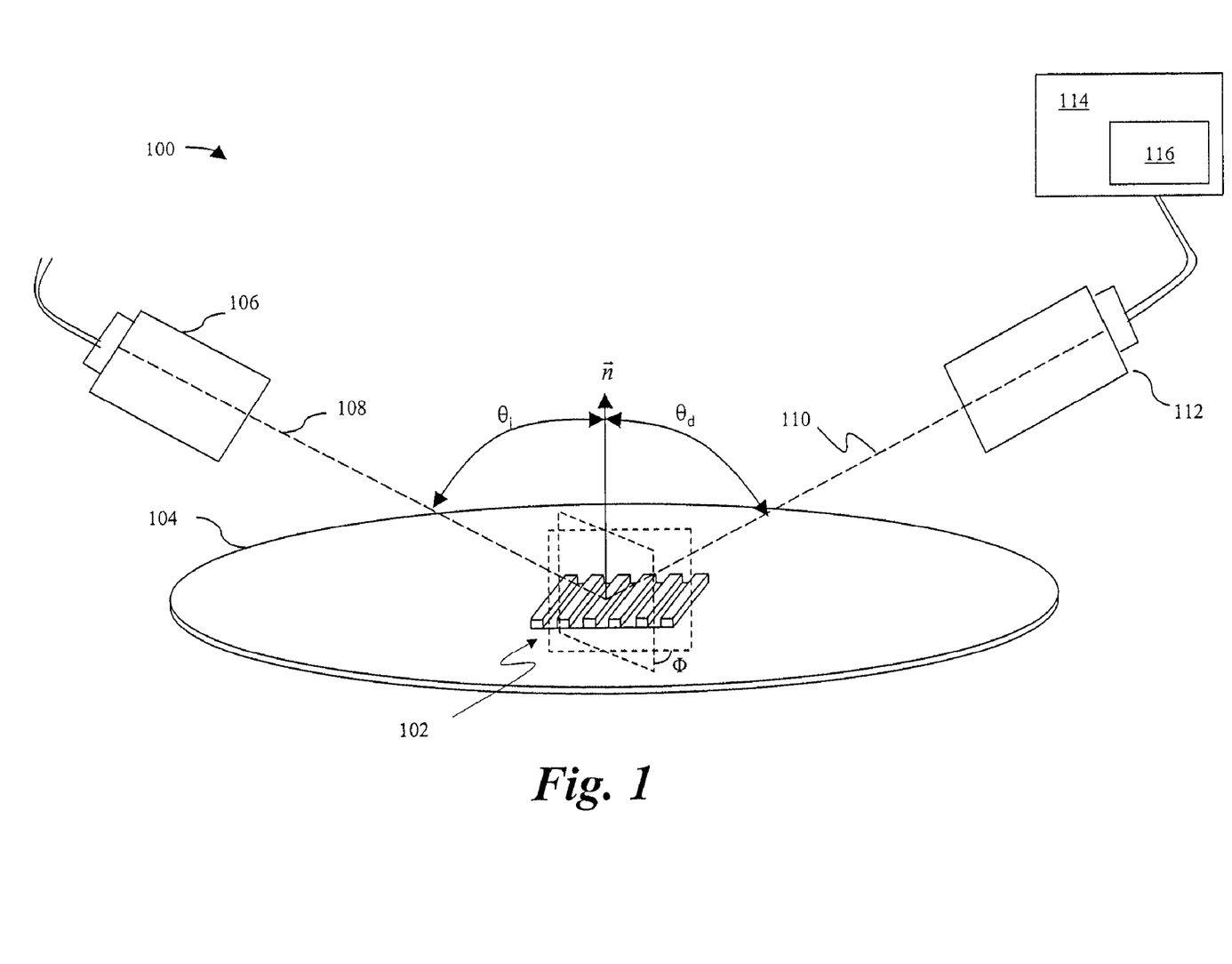
FIG. 1 depicts an exemplary optical metrology system.

With reference to FIG. 1, an optical-metrology system 100 can be used to determine the profile of periodic grating 102 formed on wafer 104. As described earlier, periodic grating 102 can be formed in test areas on wafer 104. For example, periodic grating 102 can be formed adjacent to a device formed on wafer 104. Alternatively, periodic grating 102 can be formed in an area of the device that does not interfere with the operation of the device or along scribe lines on wafer 104.

As depicted in FIG. 1, optical-metrology system 100 can include an electromagnetic source 106 and a detector 112. Periodic grating 102 is illuminated by an incident beam 108 from source 106. In the present exemplary embodiment, incident beam 108 is directed onto periodic grating 102 at an angle of incidence $\theta_i$ with respect to normal $\vec{n}$ of periodic grating 102. Diffracted beam 110 leaves at an angle of $\theta_d$ with respect to normal $\vec{n}$ and is received by detector 112.

To determine the profile of periodic grating 102, optical-metrology system 100 includes a processing module 114, which converts diffracted beam 110 received by detector 112 into a diffraction signal (i.e., a measured-diffraction signal). Processing module 114 then compares the measured-diffraction signal to simulated-diffraction signals stored in a library 116. Each simulated-diffraction signal in library 116 can be associated with a hypothetical profile. Thus, when a match is made between the measured-diffraction signal and one of the simulated-diffraction signals in library 116, the hypothetical profile associated with the matching simulated-diffraction signal can be presumed to represent the actual profile of periodic grating 102.

As described above, in conventional optical metrology, multiple periods of periodic grating 102 are typically illuminated and thus the determined profile for periodic grating 102 is based on an average representation of the illuminated periods. As described below, in one exemplary embodiment, optical-metrology system 100 can be used to determine the profile of a single period of periodic grating 102. Moreover, optical-metrology system 100 can be used to determine the profile of various types of single features formed on wafer 104, such as a line, space, contact hole, dot, and the like.

Figure 2:
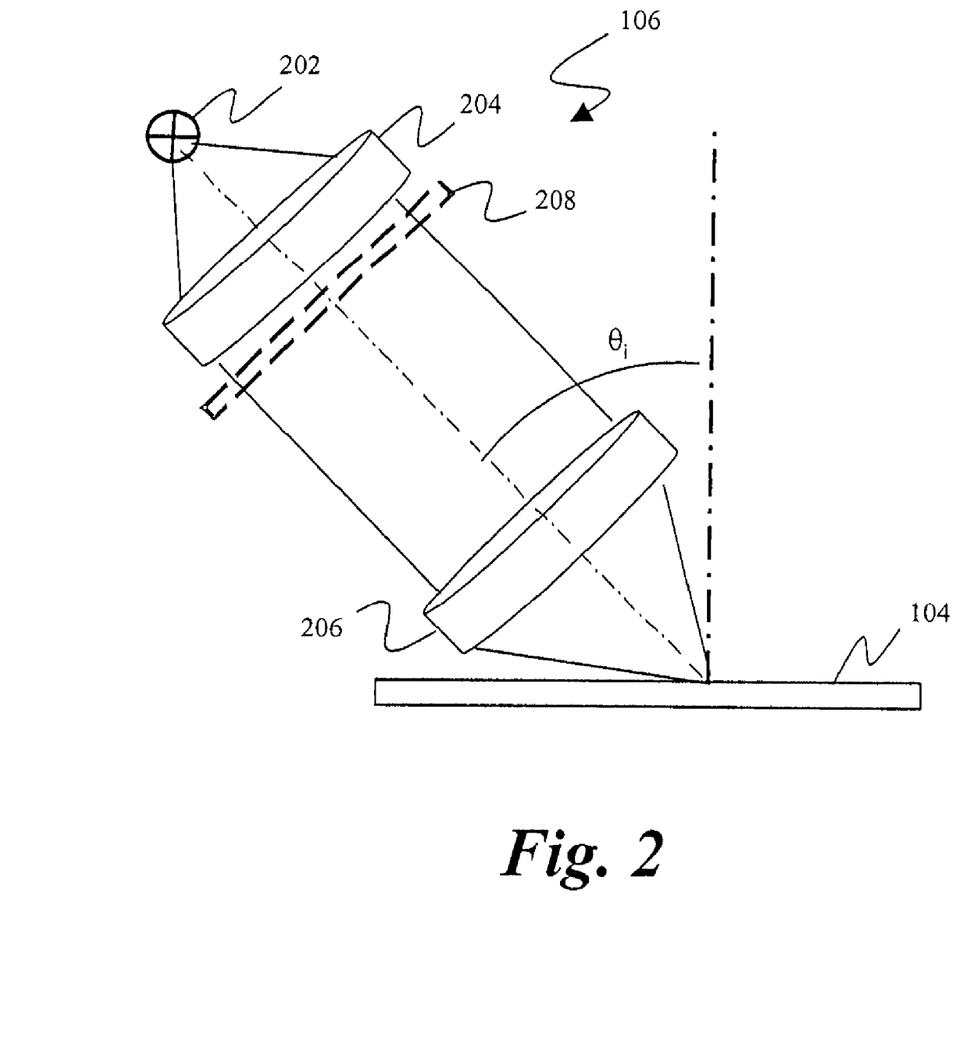
FIG. 2 depicts an exemplary source.

More particularly, source 106 can be configured to generate a beam to use in determining the profile of a single feature formed on wafer 104. With reference to FIG. 2, in one exemplary embodiment, source 106 can include a light source 202, a collimator 204, and a focusing lens 206. In the present exemplary embodiment, to determine the profile of a single feature formed on wafer 104, focusing lens 206 is configured to have a numerical aperture of greater than $\lambda/2d$, where $\lambda$ corresponds to the wavelength of the light being used and d corresponds to the distance between the feature of interest and an adjacent feature. It should be noted that focusing lens 206 can be custom made or adapted from various existing types of lenses, such as compact-disc pick-up lens, microscope objectives, monomode optical fiber, and the like.

For example, as described above, the single feature can be a single period of periodic grating 102 (FIG. 1). In this example, d corresponds to the pitch of periodic grating 102 (FIG. 1). For the sake of example, assume that the pitch and thus d is about 500 nm. Also assume for the sake of example that a wavelength of 633 nm is used. As such, focusing lens 206 is configured to have a numerical aperture of greater than about 0.6. It should be noted that if the single feature is a line, then d can correspond to the distance between the line and an adjacent line (e.g., the distance between the centers of two adjacent lines).

As depicted in FIG. 2, source 106 can also include a filter 208. Additionally, source 106 can include an automatic focus control system and positioning system (not shown) to reduce blurring and center the reference field.

Figure 3:
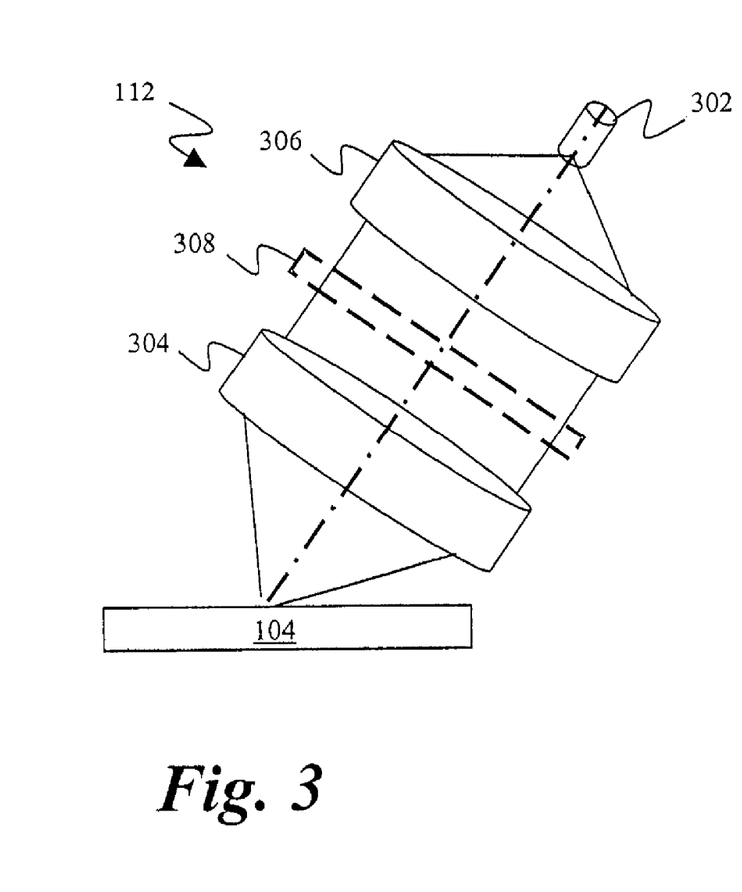
FIG. 3 depicts an exemplary detector.

With reference now to FIG. 3, in one exemplary embodiment, detector 112 includes a photo-detector 302, a collimator 304, and a focusing lens 306. In the present embodiment, diffracted beams are collected and directed onto photo-detector 302 using collimator 304 and focusing lens 306. As noted above, the focusing aperture of the illumination (i.e., the numerical aperture of focusing lens 206 of FIG. 2) and the collecting aperture of the detection (i.e., the numerical aperture of focusing lens 306) can be the same or different. Additionally, the aperture shapes can be the same or different.

In the present embodiment, an optical signature can be obtained by scanning the incidence angle of the incoming diffracted beam. For example, the incidence angle can be varied through a range by rotating the specimen being measured (e.g., wafer 104), moving source 106 (FIG. 2) and/or detector 112, or using scanning mirrors.

Alternatively, an optical signature can be obtained by scanning the wavelength of the incoming diffracted beam. For example, the incident light can be tuned by a monochromator through a spectral range, or white light can be used that is spectrally decomposed in the detection path.

As described below, an optical signature can also be obtained by scanning across the single feature. It should be noted that the optical signature can be obtained by one or more combinations of scanning the incidence angle, wavelength of the incoming diffracted beam, and/or across the single feature.

Additionally, as depicted in FIG. 3, detector 112 can include a filter 308 that can generate a weight summation by influencing amplitude as well as phase of an individual diffracted beam. More particularly, the scattering directions can be weighted and the filter function can be expressed as $A(\Theta_s) \exp^{\Phi(\Theta)}$. Thus, in this manner, phase impacts can be reflected in the intensity signal. Additionally, by adapting filter 308 to the type of specimen being used, the sensitivity of the measurements obtained can be increased.

Figure 4:
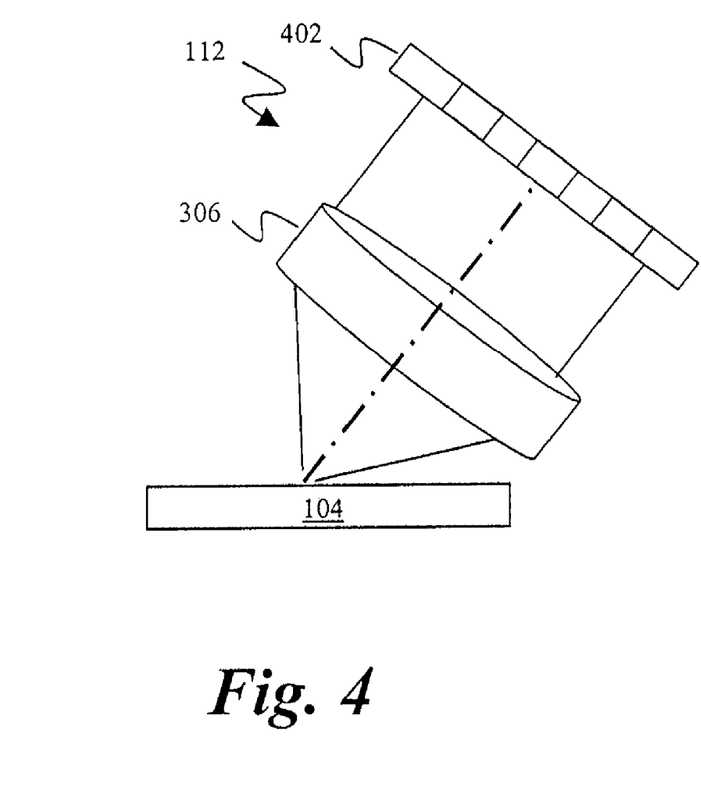
FIG. 4 depicts another exemplary detector.

With reference now to FIG. 4, in another exemplary embodiment, detector 112 includes a focusing lens 306 and a detector array 402. It should be noted that the focusing aperture of the illumination (i.e., the numerical aperture of focusing lens 206 of FIG. 2) and the collecting aperture of the detection (i.e., the numerical aperture of focusing lens 306) can be the same or different. Additionally, the aperture shapes can be the same or different.

In the present embodiment, each cell of detector array 402 can be configured to receive information from a certain scattering direction (i.e., angle). An optical signature can then be obtained from this angular information. Additionally, spectral information can be obtained by tuning a monochromatic light source through a wavelength range. Alternatively, spectral information can be obtained by illuminating with a broadband light source and inserting a dispersion element in the detection path. For example, the dispersion can be performed in a sagittal plane. Thus, one coordinate of a 2 dimension detector array 402 can be assigned to the scattering angle and the other to the color.

In another exemplary embodiment, an optical signature can be obtained for the feature by scanning the focused beam across the feature. It should be noted that the optical signature can be obtained solely by scanning across the feature. Alternatively, as noted above with reference to the embodiment of detector 112 in FIG. 3, it should be noted that the optical signature can be obtained by one or more combinations of scanning the incidence angle, wavelength of the incoming diffracted beam, and/or across the single feature. With reference to the embodiment of detector 112 in FIG. 4, it should be noted that the optical signature can be obtained from the angular information and scanning across the feature.

With reference to FIG. 1, the feature can be scanned by moving wafer 104, moving source 106 and detector 112, and/or using scanning mirrors. As the feature is scanned, data can be collected at discrete intervals, which corresponds to a sampling rate. Thus, the resolution of the optical signature obtained can depend, in part, on the sampling rate used.

Figure 5:
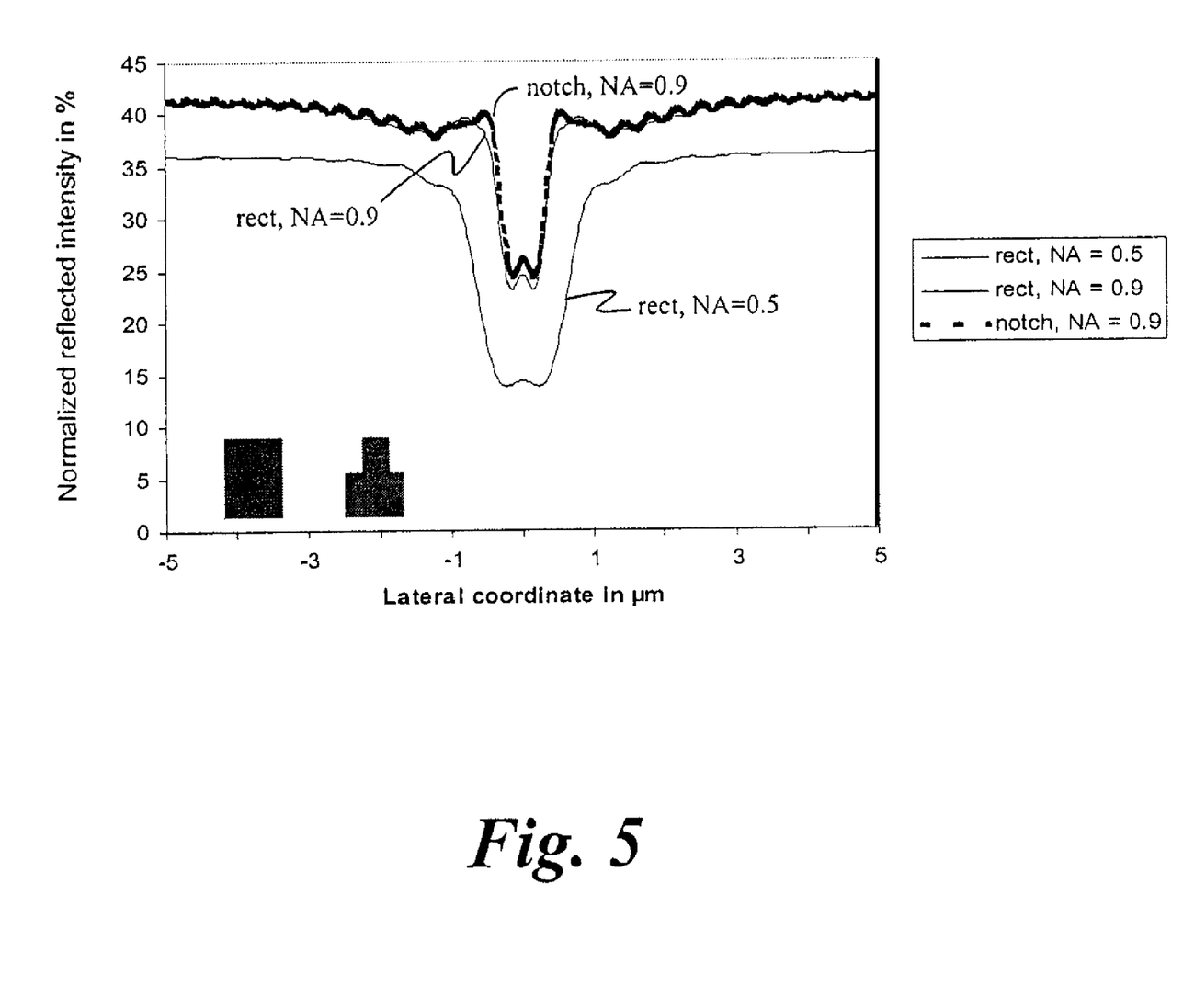
FIG. 5 depicts a graph of various exemplary optical signatures.

For example, FIG. 5 depicts optical signatures of diffracted light scanning across a 0.4 microns wide resist line having a height of 0.7 microns formed on a silicon substrate. The optical signatures depicted in FIG. 5 were modeled with a nearly continuous sampling rate. It should be noted, however, that various sampling rates can be used to obtain and model the optical signatures. However, as can be seen from FIG. 5, the greater the sampling rate, the greater the number of data points, and thus the greater the resolution of the optical signatures.

Additionally, the optical signatures depicted in FIG. 5 were modeled assuming a circular illumination and detection aperture. As depicted in FIG. 5, an optical signature was modeled for a line having a rectangular profile at a numerical aperture (NA) of 0.5 and 0.9. In FIG. 5, for the sake of clarity, the optical signature for a line having a rectangular profile at a numerical aperture (NA) of 0.5 has been shifted down by about 5% in normalized reflected intensity. As can also be seen from FIG. 5, increasing the numerical aperture increases the resolution (i.e., as the slope steepness increases, the image is less blurred). Furthermore, an optical signature was modeled for a line having a notched profile at a numerical aperture (NA) of 0.9. As can be seen from FIG. 5, the notched profile generates a distinctive optical signature as compared to the rectangular profile. Thus, optical signatures can be used to determine the profile shape of features.

Figure 6:
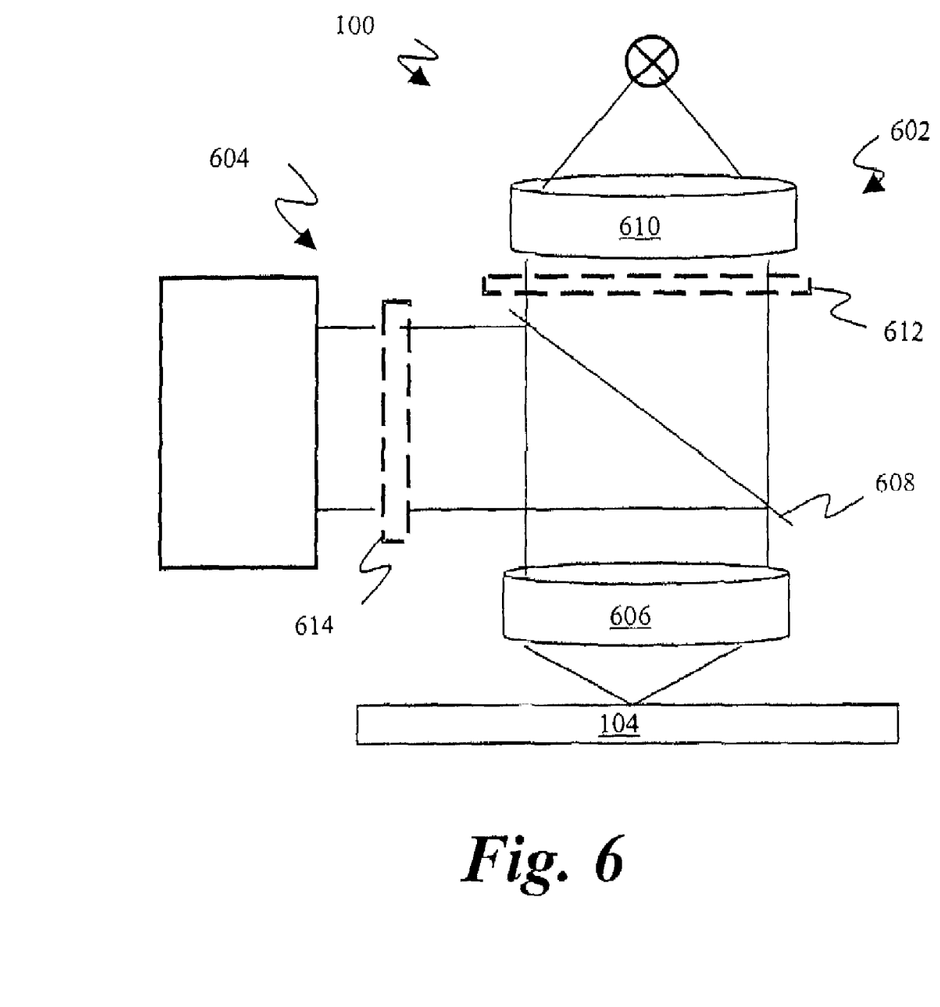
FIG. 6 depicts an exemplary source and detector.

With reference now to FIG. 6, in still another exemplary embodiment, optical metrology system 100 includes a semi-transparent beam splitter 608 to separate the excitation and detection channel of source 602 and detector 604. In the present embodiment, source 602 and detector 604 use a single focusing lens 606 having a high numerical aperture. Source 602 also includes a collimator 610. Source 602 and detector 604 can also include filters 612 and 614, respectively.

Additionally, detector 604 can include a single photo-detector 302 (FIG. 3) or a detector array 402 (FIG. 4). Thus, when a single photo-detector 302 (FIG. 3) is used, an optical signature can be obtained by scanning the incidence angle and/or wavelength of the incoming diffracted beam. When detector array 402 (FIG. 4) is used, an optical signature can be obtained by obtaining the angular information obtained from the cells of detector array 402 (FIG. 4). Furthermore, an optical signature can be obtained by scanning the focused beam across the feature.

Figure 7:
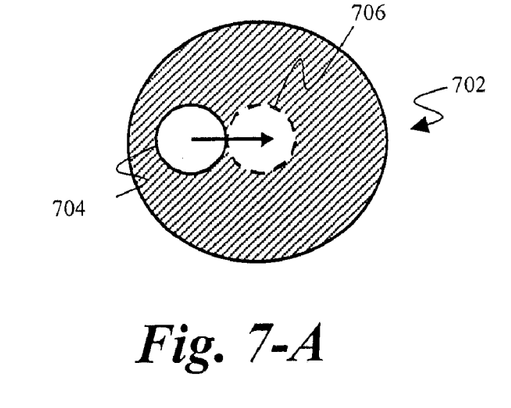
Figure 8:
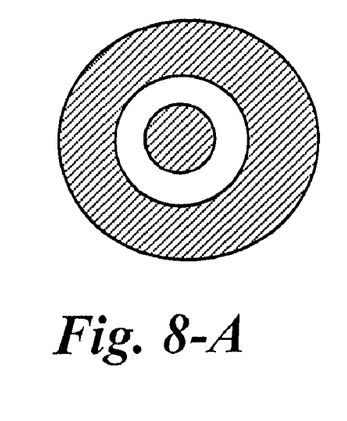

Additionally, in the present embodiment, one or more pupil stops can be used in the pupil plane to produce oblique incidence. For example, pupil stops can be placed in place of filters 612 and 614 in FIG. 6. With reference to FIGS. 7-A and 7-B, pupil stops 702 and 708 can be positioned in place of filters 612 and 614 (FIG. 6), respectively. Pupil stops 702 and 708 include de-centered pupil holes 704 and 710, respectively. Thus, in this configuration, the effective numerical aperture ($NA_{eff}$) is defined by:

$$NA_{eff} = \frac{d_s}{d_p} \cdot NA_P$$

where, $NA_p$ is the numerical aperture of the full pupil, $d_p$ the pupil diameter, and $d_s$ is the diameter of the moving hole in the pupil. As described above, for use in determining the profile of a single feature, $NA_{eff}$ is greater than $\lambda/2d$.

The de-center offset for both pupil holes 704 and 710 can be the same in x and y direction. Additionally, the de-center distance $r_{dec}$ of pupil hole 704 determines the principal angle of incidence (polar and azimuthal). The polar angle of incidence can be determined by:

$$\theta = a\sin\left(\frac{2r_{dec}}{d_p} \cdot NA_P\right)$$

Pupil stops 702 and 708 can then be shifted synchronously to scan through the incidence angle. For example, as depicted in FIGS. 7-A and 7-B, pupil stops 702 and 708 can be shifted in the direction indicated by the arrows until pupil holes 704 and 710 reach their normal angle positions 706 and 712, respectively.

It should be noted that pupil stops 702 and 708 can include various pupil shapes in addition to simple holes, such as annular, quadrupole, and the like. Additionally, the shapes of the illumination stop (i.e., pupil stop 702) and detection stop (i.e., pupil stop 708) can differ. For example, FIG. 8-A depicts an illumination stop having an annular pupil, and FIG. 8-B depicts a detection stop having a circular pupil.

With reference to FIG. 1, the obtained optical signature (i.e., the measured optical signature) can be compared to simulated optical signatures stored in a library 116. When a match is made between the measured optical signature and one of the simulated optical signatures in library 116, the hypothetical profile associated with the matching simulated optical signature can be presumed to represent the actual profile of the feature being examined on wafer 104.

In one exemplary embodiment, the simulated-optical signatures in library 116 can be generated using various modal methods, such as rigorous coupled wave analysis (RCWA), Green Integral Method (GIM), and the like.

For example, efficiencies or complex amplitudes of various diffraction orders, either propagating or evanescent, can be simulated and obtained using RCWA. The angular discretization, i.e., the discretization in the β-space (lateral wave vector component), can be determined by the grating equation:

$$\beta_m = \beta_0 + m \cdot \frac{\lambda}{d}$$

with $\beta_0$=n sin θ (for classical mount), m=diffraction order, d=distance between the feature and an adjacent feature, θ=polar angle of incidence, and λ=wavelength.

These diffraction orders can be referred to as angular- or β-spectrum. Moreover, a modal method can yield a full (complex) diffraction matrix when the diffraction matrix is made accessible for further processing. This diffraction matrix can be obtained for both reflection and transmission, and can couple all outgoing diffraction orders, i.e., the outgoing β-spectrum to the possible (permitted by the grating equation) incoming directions. In particular, for plane wave excitation, only one incident direction may be of interest. In this case, only a portion of the full information of the diffraction matrix may be used. This feature can be represented in the following vector-matrix representation:

$$(\tilde{A})_o = \sum_{i=1}^{N} (r)_{o,i} \cdot (\tilde{A})_i \qquad (1)$$

Here, $(\tilde{A})_o$ is the o-th element of a column vector that contains the outgoing spectrum, $(\tilde{A})_i$ is the i-th element of a column vector that contains the incoming spectrum and $(r)_{o,i}$ is the o,i-th element of the diffraction matrix in reflection. N is the truncation number, i.e., the total number of diffraction orders involved in the RCWA-computation. For transmission, the matrix r is replaced by the transmission matrix t.

From formula (1), it can be determined that plane wave excitation means that there is only one non-zero element in $(\tilde{A})_i$, namely the element assigned to the zero order wave-vector component $\beta_0$. This means a projection of the corresponding column out of the diffraction matrix results in a column vector $(\tilde{A})_o$ that contains the complex amplitudes for every diffraction order for plane wave incidence.

Additionally, in accordance with the concept of angular spectrum presentation of plane waves in wave optics, every wave-front with known complex amplitude distribution can be decomposed in a spectrum of plane waves. The decomposition procedure is identical with a complex Fourier transformation:

$$\tilde{A}(\vec{\beta}) = \int_{\vec{r}} A(\vec{r}) \cdot \exp(j\vec{\beta}\vec{r}) \qquad (2)$$

Here, A(r) is the complex amplitude of the wave and r is a position vector. For numerical reasons the integral is replaced by a sum. This means that the integration boundaries become finite. Actually, the physical problem is embedded into a finite range, which will be referred to as a super-period P. Due to spatial confinement, the previous continuous spectrum turns into a discrete spectrum. Thus, the continuous function $\tilde{A}(\vec{\beta})$ becomes a discrete function that can be expressed by a vector comprising the elements $(\tilde{A})_m$. Applying this approach, an arbitrary non-periodic pattern can be treated correctly.

Thus, simulated optical signatures of the diffraction of focused beam can be generated and obtained as follows:

First, the incident spectrum is computed from the distribution of the complex amplitude of a given incident wave by means of formula (2). In optical modeling, a Gaussian beam and a circular beam with an Airy-disc diffraction spot are two models that are widely used as idealized beam shapes for a single mode laser and for a diffraction-limited optical system in connection with a point source illumination. A Gaussian beam for example having a waist diameter $2w_0$ has the following angular spectrum:

$$\tilde{A}_m = \tilde{A}_0 \cdot \exp\left(-\frac{1}{2}\left(\frac{2\pi}{\lambda}\beta_m w_0\right)^2\right) \cdot \exp\left(j\frac{2\pi}{\lambda}\beta_m x_0\right) \cdot \exp\left(-j\frac{2\pi}{\lambda}\alpha_m z_0\right) \quad (3)$$

where, $\tilde{A}_0$ is the amplitude of the zero-order plane wave component, $\beta_m$ is the lateral wave vector component, and $\alpha_m$ is the normal wave vector component of the m-th order. The additional exponential terms express an offset of the beam relative to its "zero"-position in lateral direction (the beam center is offset to the coordinate $x_0$) and in vertical direction (defocus is $z_0$). An Airy disc (e.g., the intensity distribution figure in the focus plane of a diffraction limited optical system) entails a simple circ-function as spectrum.

Second, the full diffraction matrix r (or t) is computed by means of a rigorous diffraction method, such as RCWA, GIM, and the like.

Third, the diffraction matrix is multiplied with the column vector of the incident spectrum resulting in the column vector of the outgoing (diffracted) spectrum.

And next, from the elements of the out-vector, either a total detector amplitude or intensity can be computed (see equation 4 below and FIG. 3) or the elements can be regarded as direction amplitudes/intensities of the scattered beam (FIG. 4).

Additionally, a detector-signal can be obtained by multiplying the vector of the outgoing spectrum by a vector $(D)_0$ that embodies the (complex) detector function (including of course possible filters, phase retarders etc.). This yields the complex amplitude $A_d$ of the integrated signal at the detector:

$$A_d = \sum_{i=1}^{N} (D)_o \cdot (\tilde{A})_o = \sum_{o=1}^{N} (D)_o \cdot \sum_{i=1}^{N} (r)_{o,i} \cdot (\tilde{A})_i \quad (4)$$

Finally, the intensity is obtained by taking the square: $I_d \propto A_d \cdot A_d^*$.

As described above, with reference to FIG. 3, in one exemplary embodiment, detector 112 includes focusing lens 306 configured to collect and direct diffracted beams onto photodetector 302. For this exemplary embodiment, a maximum numerical aperture value can be obtained by averaging the intensity over the numerical aperture of focusing lens 306 and comparing this value with the plane wave response of the principal (i.e., central) "ray" of the focused beam. A normalized deviation is obtained. The maximum numerical aperture value can then be determined by relating the normalized deviation to an allowed error limit.

Figure 9:
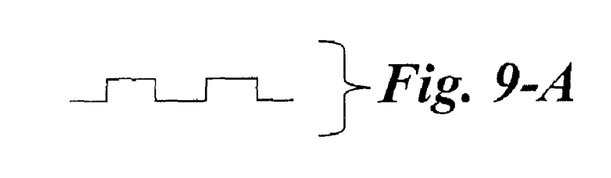
FIG. 9A depicts an exemplary periodic pattern.
FIGS. 9B and 9C depict exemplary diffraction matrices of the exemplary periodic pattern depicted in FIG. 9A.
Figure 10:
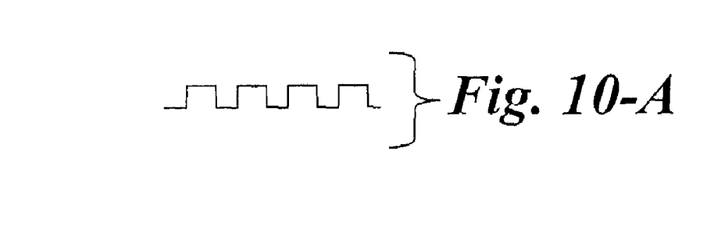
FIG. 10A depicts an exemplary periodic pattern.
FIGS. 10B and 10C depict exemplary diffraction matrices of the exemplary periodic pattern depicted in FIG. 10A.

Additionally, as described above, the diffraction matrix for a periodic pattern can be embedded in a super-period. As depicted in FIGS. 9-A, 9-B, and 9-C, a periodic pattern (FIG. 9-A) can cause strong diagonal lines that are assigned to certain diffraction orders in the diffraction matrix (FIGS. 9-B and 9-C). As depicted in FIGS. 10-A, 10-B, and 10-C, at constant wavelength, when the pitch of the periodic pattern increases (FIG. 10-A), the diffraction matrix becomes denser (FIGS. 10-B and 10-C). As also described above, the diffraction matrices are excited with an input spectrum (i.e., the matrix multiplication of equation 1 is performed).

As can be seen from FIGS. 9-B, 9-C, 10-B, and 10-C, the resulting outgoing spectrum excited by a focused incident wave will be affected only by the zero-th order (i.e., the main diagonal of the matrices) as long as the incident spectrum (i.e., the doubled numerical aperture of the incident beam) is not wider than the modal distance $\lambda/d$. However, conventional optical metrology for use with periodic gratings is typically characterized by the condition:

$$2NA = 2n \cdot \sin(u) \leq \frac{\lambda}{d} \quad (5a)$$

where u is the aperture angle.

In contrast, as described above, optical metrology for use with single features can be characterized by the condition:

$$2NA = 2n \cdot \sin(u) > \frac{\lambda}{d} \quad (5b)$$

When this condition is met, the incident spectrum begins to cover neighboring marginal diagonals. Numerically, this means that the resulting component (or plane wave) of the outgoing wave has to be computed as shown in equation (1), namely by coherent addition of the contributions from more than components of the incidence spectrum. From a physical point of view, this means interference. The optical meaning of high numerical aperture illumination in combination with a low $\lambda/d$ ratio is that a single feature of the pattern can be addressed while ignoring widely the surrounding.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching.

We claim:

1. A system for illuminating a single feature formed on a wafer, the system comprising:
   a source configured to generate a beam of light, the source having a first pupil stop with a first pupil hole that is de-centered with respect to the first pupil stop, wherein the first pupil stop has an effective numerical aperture greater than the wavelength of the light used divided by twice the distance between the single feature and an adjacent feature;
   a detector having a second pupil stop with a second pupil hole that is de-centered with respect to the second pupil stop, wherein the second pupil stop has an effective numerical aperture greater than the wavelength of the light used divided by twice the distance between the single feature and an adjacent feature;
   a focusing lens; and
   a beam splitter disposed adjacent to the focusing lens, wherein the beam of light generated by the source is focused on the single feature through the beam splitter and the focusing lens, and diffracted beams of light from the single feature are received in the detector through the focusing lens and the beam splitter.

2. The system of claim 1, wherein the first pupil stop and the second pupil stop are configured to synchronously shift from an initial incidence angle to a final incidence angle.

3. The system of claim 1, wherein the first pupil stop and the second pupil stop have common shapes.

4. The system of claim 1, wherein the first pupil stop and the second pupil stop having different shapes.

5. The system of claim 1, wherein the first pupil stop has a circular shape.

6. The system of claim 1, wherein the first pupil stop has an annular shape.

7. The system of claim 1, wherein the effective numerical aperture of the first pupil stop is a ratio of diameters of the first pupil hole and the first pupil stop multiplied by numerical aperture of the first pupil stop without the first pupil hole.

8. The system of claim 1, wherein the effective numerical aperture of the second pupil stop is a ratio of diameters of the second pupil hole and the second pupil stop multiplied by numerical aperture of the second pupil stop without the second pupil hole.

9. The system of claim 1, wherein the detector includes a single photo-detector.

10. The system of claim 9, wherein the detector includes a filter configured to generate a weight summation of the diffracted beams.

11. The system of claim 1, wherein the detector includes a detection array having a plurality of detection cells.

12. The system of claim 11, wherein each detection cell is configured to receive information from a specific scattering direction.

13. The system of claim 1, wherein the detection array is a two dimensional array with one dimension assigned to scattering angles and another dimension assigned to color.

14. A system for illuminating a single feature formed on a wafer, the system comprising:
a source configured to generate a beam of light, the source having a first pupil stop with a first pupil hole that is de-centered with respect to the first pupil stop, wherein the first pupil stop has an effective numerical aperture greater than the wavelength of the light used divided by twice the distance between the single feature and an adjacent feature;
a detector having a second pupil stop with a second pupil hole that is de-centered with respect to the second pupil stop, wherein the second pupil stop has an effective numerical aperture greater than the wavelength of the light used divided by twice the distance between the single feature and an adjacent feature;
a focusing lens;
a beam splitter disposed adjacent to the focusing lens, wherein the beam of light generated by the source is focused on the single feature through the beam splitter and the focusing lens, and diffracted beams of light from the single feature are received in the detector through the focusing lens and the beam splitter; and
a processor connected to the detector configured to determine the profile of the single feature based on the diffracted beams of light received by the detector.

15. The system of claim 14, wherein the first pupil stop and the second pupil stop are configured to synchronously shift from an initial incidence angle to a final incidence angle.

16. The system of claim 14, wherein the effective numerical aperture of the first pupil stop is a ratio of diameters of the first pupil hole and the first pupil stop multiplied by numerical aperture of the first pupil stop without the first pupil hole.

17. The system of claim 14, wherein the processor is configured to compare an optical signature obtained from the diffracted beams of light to a set of simulated optical signatures, wherein each simulated optical signature corresponds to a hypothetical profile of the single feature.

18. A method of illuminating a single feature formed on a wafer, the system comprising:
generating a beam of light using a source, the source having a first pupil stop with a first pupil hole that is de-centered with respect to the first pupil stop, wherein the first pupil stop has an effective numerical aperture greater than the wavelength of the light used divided by twice the distance between the single feature and an adjacent feature;
focusing the beam of light generated by the source on the single feature using a focusing lens;
directing diffracted beams of light received from the single feature through the focusing lens to a detector using a beam splitter disposed adjacent to the focusing lens, the detector having a second pupil stop with a second pupil hole that is de-centered with respect to the second pupil stop, wherein the second pupil stop has an effective numerical aperture greater than the wavelength of the light used divided by twice the distance between the single feature and an adjacent feature; and
determining the profile of the single feature based on the diffracted beams of light received by the detector.

19. The method of claim 18, further comprising:
synchronously shifting the first and second pupil stops from an initial incidence angle to a final incidence angle.

20. The method of claim 18, wherein determining the profile of the single feature comprises:
obtaining an optical signature from the diffracted beams of light; and
comparing the obtained optical signature to a set of simulated optical signatures, wherein each simulated optical signature corresponds to a hypothetical profile of the single feature.

* * * * *